US008187859B2

(12) United States Patent
Van Vuuren et al.

(10) Patent No.: US 8,187,859 B2
(45) Date of Patent: May 29, 2012

(54) MODULATING UREA DEGRADATION IN WINE YEAST

(75) Inventors: Hendrik Jurgens Jansen Van Vuuren, Lions Bay (CA); Aline Lonvaud, Bordeau (FR); Joana Coulon, Ghent (BE); Debra Inglis, Virgil (CA)

(73) Assignee: The University of British Columbia, Vancouver, B.C. (CA)

( * ) Notice: Subject to any disclaimer, the term of this patent is extended or adjusted under 35 U.S.C. 154(b) by 18 days.

(21) Appl. No.: 10/494,742

(22) PCT Filed: Nov. 6, 2002

(86) PCT No.: PCT/CA02/01719
§ 371 (c)(1),
(2), (4) Date: Nov. 22, 2004

(87) PCT Pub. No.: WO03/040379
PCT Pub. Date: May 15, 2003

(65) Prior Publication Data
US 2005/0069885 A1 Mar. 31, 2005

Related U.S. Application Data

(60) Provisional application No. 60/330,993, filed on Nov. 6, 2001.

(51) Int. Cl.
*C12N 1/00* (2006.01)
*C12N 9/88* (2006.01)
*C12N 1/20* (2006.01)
*C12Q 1/68* (2006.01)
*C12P 7/06* (2006.01)
*C07H 21/04* (2006.01)

(52) U.S. Cl. ....... 435/254.21; 435/6; 435/161; 435/232; 435/252.3; 536/23.2

(58) Field of Classification Search .................. 435/232, 435/252.3, 254.21, 161
See application file for complete search history.

(56) References Cited

U.S. PATENT DOCUMENTS

| | | | |
|---|---|---|---|
| 4,373,071 A | 2/1983 | Itakura | |
| 4,401,796 A | 8/1983 | Itakura | |
| 4,458,066 A | 7/1984 | Caruthers et al. | |
| 4,598,049 A | 7/1986 | Zelinka et al. | |
| 6,140,108 A | 10/2000 | Mortimer et al. | |
| 6,159,725 A | 12/2000 | Klaassen et al. | |
| 6,159,759 A | 12/2000 | Klassen et al. | |
| 6,274,311 B1 | 8/2001 | Grobler et al. | |

FOREIGN PATENT DOCUMENTS

| | | |
|---|---|---|
| JP | 63-226274 | 9/1988 |
| JP | 03-072869 | 3/1991 |
| JP | 04-020282 | 1/1992 |
| JP | 05 244959 A | 9/1993 |

OTHER PUBLICATIONS

Albert, M., et al., "Effect of diammonium phosphate additions on the production of ethyl carbamate during wine fermentations," *Am. J. Enol. Vitic.* 51(3):300 (2000).
Altschul, S., et al., "Basic local alignment search tool," *J. Mol. Biol.* 215(3):403-410 (Oct. 1990).
Altschul, S., et al., "Gapped BLAST and PSI-BLAST: a new generation of protein database search programs," *Nucleic Acids Res.* 25(17):3389-3402 (Sep. 1997).
Cooper, T., et al., "Structural analysis of the dur loci in *S. cerevisiae*: two domains of a single multifunctional gene, "*Genetics* 94(3):555-580 (Mar. 1980).
Cox, K., et al., "*Saccharomyces cerevisiae* GATA sequences function as TATA elements during nitrogen catabolite repression and when Gln3p is excluded from the nucleus of overproduction of Ure2p," *J. Biol. Chem.* 275(23):17611-17618 (Mar. 2000).
Eisenberg, D. et al., "Analysis of membrane and surface protein sequences with the hydrophobic moment plot," *J. Mol. Biol.* 179(1):125-142 (Oct. 1984).
Feldmann, H., et al., "Complete DNA sequence of yeast chromosome II," *EMBO J.* 13(24):5795-5809 (Dec. 1994).
Gietz, R.D., et al., "Studies on the transformation of intact yeast cells by the LiAc/SS-DNA/PEG procedure," *Yeast* 11:355-360 (1995).
Genbauffe, F., et al., "Induction and repression of the urea amidolyase gene in *Saccharomyces cerevisiae*," *Mol. Cell. Biol.* 6(11):3954-3964 (Nov. 1986).
Genbauffe, F., et al., "The urea amidolyase (*DUR1,2*) gene of *Saccharomyces cerevisiae*," *DNA Sequence J. DNA Sequencing Mapping* 2(1):19-32 (1991).
Goffeau, A., et al., (Direct Submission), NCBI Accession No. NP_009767 (GI 6319685), Oct. 14, 2004.
Goffeau, A., et al., "Life with 6000 genes," *Science* 274(5287):546 (1996).
Hienikoff, S., et al.. "Amino acid substitution matrices from protein blocks," *Proc. Natl. Acad. Sci. USA* 89(22)10915-10919 (Nov. 1992).
Henschke, P., et al., "Yeasts—Metabolism of Nitrogen Compounds," in *Wine Microbiology and Biotechnology*, pp. 77-164, G.H. Fleet (ed.), Harwood Academic Publishers: Chur, CH (1993).
Hoffmann, W., "Molecular characterization of the *CAN1* locus in *Saccharomyces cerevisiae*," *J. Biol. Chem.* 260(21):11831-11837 (Sep. 1985).
Jauniaux, J.-C., et al., "*GAP1*, the general amino acid permease gene of *Saccharomyces cerevisiae*: Nucleotide sequence, protein similarity with the other bakers yeast amino acid permeases, and nitrogen catabolite repression," *Eur. J. Biochem.* 190(1):39-44 (May 1990).
Maitz, G., et al., "Purification and properties of the allophanate hydrolase from *Chlamydomonas reinhardii*," *Biochim. Biophys. Acta* 714:486-491 (1982).
Middelhoven, W.J., et al., "The pathway of arginine breakdown in *Saccharomyces cerevisiae*," *Biochim. Biophys. Acta* 93:650-652 (1964).

(Continued)

Primary Examiner — Robert Mondesi
Assistant Examiner — Iqbal H Chowdhury
(74) Attorney, Agent, or Firm — Dorsey & Whitney LLP

(57) ABSTRACT

The invention provides yeast strains transformed to reduce nitrogen catabolite repression of a gene encoding a urea degrading enzymatic activity expressed by the yeast strain under fermenting conditions. Strains of *Saccharomyces cerevisiae* are for example provided having enhanced DUR1,2 urea carboxylase-allophanate hydrolase activity under wine fermenting conditions.

12 Claims, 7 Drawing Sheets

OTHER PUBLICATIONS

Mirvish, S., "The carcinogenic action and metabolism of urethan and n-hydroxyurethan," *Adv. Cancer Res.* 11:1-42 (1968).

Needleman, S., et al., "A general method applicable to the search for similarities in the amino acid sequence of two proteins," *J. Mol. Biol.* 48(3):443-453 (Mar. 1970).

Negritto, M.T., et al., "Influence of DNA sequence identity on efficiency of targeted gene replacement," *Mol. Cell. Biol.* 17(1):278-286 (Jan. 1997).

Pearson, W. et al., "Improved tools for biological sequence comparison," *Proc. Natl. Acad. Sci USA* 85(8):2444-2448 (Apr. 1988).

Pigeau, G., *Characterization of wild-type and mutant ureases of the fission yeast Schizosaccharomyces pombe*, Brock University Cool Climate Oenology and Viticulture Institute: St. Catherines, ONT (CA) (Jun. 2002).

Rathjen, P.D., et al., "The yeast ROAM mutation—identification of the sequences mediating host gene activation and cell-type control in the yeast retrotransposon, Ty," *Nucleic Acids Res.* 15(18):7309-7324 (Sep. 1987).

Roon, R., et al., "ATP: Urea amidolyase (ADP) (*Candida utilis*)," *Methods Enzymol.* 17A:317-324 (1970).

Roon, R., et al. "Urea amidolyase. I. Properties of the enzyme from *Candida utilis*," *J. Biol. Chem.* 247(13):4107-4113 (Jul. 1972).

Rothstein, R., "Targeting, disruption, replacement, and allele rescue: integrative DNA transformation in yeast," *Methods Enzymol.* 194:281-301 (1991).

Simon, J., at al., "Homologous recombination between single-stranded DNA and chromosomal genes in *Saccharomyces cerevisiae*," *Mol. Cell. Biol* 7(7):2329-2334 (Jul. 1987).

Smith, T., et al., "Comparison in biosequences," *Adv. Appl. Math.* 2:482-489 (1981).

Sumrada, R., et al., "Urea carboxylase and allophanate hydrolase are components of a multifunctional protein in yeast," *J. Biol. Chem.* 257(15):9119-9127 (Aug. 1982).

Tijssen, P., "Overview of principles of hybridization and the strategy of nucleic acid probe assays," in *Laboratory Techniques in Biochemistry and Molecular Biology—Hybridization with Nucleic Acid Probes*, Part 1, pp. 19-78, Elsevier: New York, NY (1993).

Van Rensburg, P., et at., "Enzymes in winemaking: harnessing natural catalysts for efficient biotransformations: a review," *S. Afr. J. Enol. Viticult.* 21:52-73 (2000).

Visser, J., et al., "Engineering an acid urease for heterologous expression in *Saccharomyces cerevisiae*," *Curr. Genet.* 35(384):321 (May 1999).

Volschenk, H., et al., "Engineering pathways for malate degradation in *Saccharomyces cerevisiae*," *Nat. Biotechnol.* 15(3):253-257 (Mar. 1997).

Winzeler, E., et al., "Functional characterization of the *S. cerevisiae* genome by gene deletion and parallel analysis," *Science* 285(5429):901-906 (Aug. 1999).

Database Geneseq 'Online' May 10, 1994, Urea Amidolyase Gene Database accession No. AAQ49460 XP02240762.

Hofman-Bang Jacob, Nitrogen Catabolite Repression in *Saccharomyces cerevisiae* vol. 12, Molecular Biotechnology, Aug. 1999, pp. 35-73.

Chisholm et al., 1992, Journal of Bacteriology, 174, 8, p. 2548.

Brock University, 2000, Online, retrieved from the internet, http://www.brocku.ca/ccovi/res/inglis7.html.

J. Brew, Soc. Japan., 1989, vol. 84, No. 6, pp. 413-417.

Journal of Fermentation and Bioengineering, 1993, vol. 75, No. 4, pp. 245-253.

S.Afr. J. Enol. Vitic., 2000, vol. 21, Special Issue, pp. 52-73.

Figure 1

```
643180  TTCGCTTTTT CTAAAATAAA GGTCCCCGCT GAAACTTCTT TGCATACAGT TCAAATATTC
643120  CACCGTTCTC TTATATGTGG GGCTGGCACT ACTTCGTATA ATTGACTATA CTATCTATAT
643060  TAGTCTTCCC ACATGTAATA GAAAGCTCGT ATGGCGCAGT GGTAGCGCAG CAGATTGCAA
                                          ━━━━━━━━━━━━━━━━━━━━━━━━━━━━━━▶ TC(GCA)B
                                          ━━━━━━━━━━━━━━━━━━━━━━━━━━━━━━▶ tRNA-Cys
643000  ATCTGTTGGT CCTTAGTTCG ATCCTGAGTG CGAGCTTCTT TTTTTTTTTG CAATCCTTAT
        ━━━━━━━━━━━━━━━━━━━━━━━━━━━━━━━━━━━━━━━━━━▶ TC(GCA)B
        ━━━━━━━━━━━━━━━━━━━━━━━━━━━━━━━━━━━━━━━━━━▶ tRNA-Cys
642940  TGAACTTTTT TTCTTGCTGC AGTCTCCTCA AAGGCAACAT GTTCTTTGCT TTTTTTCCCC
642880  AACGACGTCG AACACATTAG TCCTATGGCT TGCTGCAGAT AAGGCTACTA TGTGTATTGG
                                                                         YBR209W
        ◀━━━━━━━━━━━━━━━━━━━━━━━━━━━━━━━━━━━━━━━━━━━━━━━━━━━━━━━━━━━━━━━ Hypothetical ORF
                 P   K   S   C   I   L   S   S   H   T   N   A
642820  CAATACCCTT TTTAAAATTG GCAGATCTCT TATGGCGATC GCCGAACGCC AGGTTGTTAG
                                                                         YBR209W
        ◀━━━━━━━━━━━━━━━━━━━━━━━━━━━━━━━━━━━━━━━━━━━━━━━━━━━━━━━━━━━━━━━ Hypothetical ORF
          I   G   K   K   F   N   A   S   R   K   H   R   D   G   F   A   L   N   N   A
642760  CTAACTGCAA CGGCACGCAT CTTTGGCTGC ATTTCGCCTC ATCATTTACG CGCTTTTCCA
                                                                         YBR209W
        ◀━━━━━━━━━━━━━━━━━━━━━━━━━━━━━━━━━━━━━━━━━━━━━━━━━━━━━━━━━━━━━━━ Hypothetical ORF
          L   Q   L   P   V   C   R   Q   S   C   K   A   E   D   N   V   R   K   E   L
642700  GGCTTTTCC CCTTATCAGA TAAGATAAAA AAACGAACAA TAAATAAGCT TCAGATAAGA
                                                                         YBR209W
        ◀━━━━━━━━━━━━━━━━━━━━━━━━━━━━━━━━━━━━━━━━━━━━━━━━━━━━━━━━━━━━━━━ Hypothetical ORF
          S   K   G   R   I   L   Y   S   L   F   V   F   L   L   Y   A   E   S   L   I
642640  TAAGCAGGAA AGCGTTCCTA GCCCTACCGA GAAATGTGCG TTTATAGTTT GGTGCCTCTT
                                                                         YBR209W
        ◀━━━━━━━━━━━━━━━━━━━━━━━━━━━━━━━━━━━━━━━━━━━━━━━━━━━━━━━━━━━━━━━ Hypothetical ORF
          L   L   F   A   N   R   A   R   G   L   F   T   R   K   Y   N   P   A   E   K
642580  TCTTGATTGA CGCTCTATAA TGAAACCAAT ATGCGTTCAT TCCCCTATTT CATAGGGCAC
                                                            ◀━━━━━━━━━━━ YBR209W
        ◀━━━━━━━━━━━━━━━━━━━━━━━━━━━━━━━━━━━━━━━━━━━━━━━━━━━ Hypothetical ORF
          K   I   S   A   R   Y   H   F   W   Y   A   N   M
642520  TCTGTTCGCA GTTAGCGCAA GCCATTGAGA TAAGCACACGC AGATGTTTTG CTTTTTCCTG
642460  CTTCTTAATT TGAATCGAGC TTTGTTAGAC GTTGTTGGAA ATTGAATGTT TGTATTTAAA
642400  CACTAGAGCA GATGAGGTGT GAGATTTGTA TACTCGCTCA CTTCTGAATA TCAGGCTCTC
642340  TTAGCTAAGC TTTTTTTTTC TAGGATCATA TAGGCTCAAG TTTTTATAAG CTTATATTAA
642280  TATATCAGTG GAGCAGCTGA TATACACCAA ATTTCAATTT ACATTAATAT AAAAGATAAA
642220  AAATAGAAAT ATCTTTTTTA TAGTCACAAT AAATTTCAGT TTTGATTAAA AAATGACAGT
                                                                   ━━━━▶ DUR1,2
                                                            ◀━━━━━━━━━━━ Urea amidolyase
                                                              M   T   V
```

Figure 2 tc ccctatttca tagggcactc
-372 tgttcgcagt tagcgcaagc cattga|gata ag|acacgcag atgttttgct ttttcctgct
-350 tcttaatttg aatcgagctt tgttagacgt tgttggaaat tgaatgtttg tatttaaaca
-290 ctagagcaga tgaggtgtga gatttgtata ctcgctcact tctgaatatc aggctctctt
-230 agctaagctt ttttttttcta ggatcatata ggctcaagtt tt|tataa|gct tatattaata
-170 tatcagtgga gcagctgata tacaccaaat ttcaatttac attaa|tataa| aa|gataa|aaa
-110 atagaaatat cttttttata gtcacaataa atttcagttt tgattaaaaa atg
-50        -40        -30        -20        -10        1

SEQUENCE LISTING

```
<160> NUMBER OF SEQ ID NOS: 7

<210> SEQ ID NO 1
<211> LENGTH: 29
<212> TYPE: DNA
<213> ORGANISM: Artificial Sequence
<220> FEATURE:
<223> OTHER INFORMATION: Artificial Sequence = Primer

<400> SEQUENCE: 1
ttaaaaaaat gacagttagt tccgataca                                     29

<210> SEQ ID NO 2
<211> LENGTH: 32
<212> TYPE: DNA
<213> ORGANISM: Artificial Sequence
<220> FEATURE:
<223> OTHER INFORMATION: Artificial Sequence = Primer

<400> SEQUENCE: 2
tcgaaaaagg tatttcatgc caatgttatg ac                                 32

<210> SEQ ID NO 3
<211> LENGTH: 1020
<212> TYPE: DNA
<213> ORGANISM: Saccharomyces cerevisiae

<400> SEQUENCE: 3
tgacagtaaa aaattagttt tgactttaaa taacactgat attttttcta taaagataaa     60
aaatagaaaa tataattaca tttaactta aaccacatat agtcgacgag gtgactatat    120
aattatattc gaatattttt gaactcggat atactaggat cttttttttt cgaatcgatt   180
```

-continued

```
ctctcggact ataagtcttc actcgctcat atgtttagag tgtggagtag acgagatcac    240
aaatttatgt ttgtaagtta aaggttgttg cagattgttt cgagctaagt ttaattcttc    300 gtccttttc gttttgtaga cgcacagaat agagttaccg aacgcgattg acgcttgtct    360
cacgggatac tttatcccct tacttgcgta taaccaaagt aatatctcgc agttagttct    420
ttctccgtgg tttgatattt gcgtgtaaag agccatcccg atccttgcga aggacgaat     480 agaatagact tcgaataaat aacaagcaaa aaaatagaat agactattcc ccttttttcgg   540 accttttcgc gcatttacta ctccgctttta cgtcggtttc tacgcacggc aacgtcaatc   600
gattgttgga ccgcaagccg ctagcggtat tctctagacg gttaaaattt ttcccataac   660
ggttatgtgt atcatcggaa tagacgtcgt tcggtatcct gattacacaa gctgcagcaa   720 ccccttttt tcgtttcttg tacaacggaa actcctctga cgtcgttctt ttttttcaagt    780 tattcctaac gtttttttt ttcttcgagc gtgagtccta gcttgattcc tggttgtcta    840
aacgttagac gacgcgatgg tgacgcgta tgctcgaaag ataatgtaca cccttctgat    900
tatatctatc atatcagtta atatgcttca tcacggtcgg ggtgtatatt ctcttgccac    960
cttataaact tgacatacgt ttcttcaaag tcgcccctgg aaataaaatc tttttcgctt   1020
```

<210> SEQ ID NO 4
<211> LENGTH: 105
<212> TYPE: PRT
<213> ORGANISM: Saccharomyces cerevisiae

<400> SEQUENCE: 4

```
Met Asn Ala Tyr Trp Phe His Tyr Arg Ala Ser Ile Lys Lys Glu Ala
1               5                   10                  15

Pro Asn Tyr Lys Arg Thr Phe Leu Gly Arg Ala Arg Asn Ala Phe Leu
            20                  25                  30

Leu Ile Leu Ser Glu Ala Tyr Leu Leu Phe Val Phe Leu Ser Tyr Leu
        35                  40                  45

Ile Arg Gly Lys Ser Leu Glu Lys Arg Val Asn Asp Glu Ala Lys Cys
    50                  55                  60

Ser Gln Arg Cys Val Pro Leu Gln Leu Ala Asn Asn Leu Gln Phe Gly
65                  70                  75                  80

Asp Arg His Lys Arg Ser Ala Asn Phe Lys Lys Gly Ile Ala Asn Thr
                85                  90                  95

His Ser Ser Leu Ile Cys Ser Lys Pro
            100                 105
```

<210> SEQ ID NO 5
<211> LENGTH: 375
<212> TYPE: DNA
<213> ORGANISM: Saccharomyces cerevisiae

<400> SEQUENCE: 5

```
tcccctattt catagggcac tctgttcgca gttagcgcaa gccattgaga taagacacgc     60
agatgttttg cttttcctg cttcttaatt tgaatcgagc tttgttagac gttgttggaa    120
attgaatgtt tgtatttaaa cactagagca gatgaggtgt gagatttgta tactcgctca    180
cttctgaata tcaggctctc ttagctaagc ttttttttc taggatcata taggctcaag    240
tttttataag cttatattaa tatatcagtg gagcagctga tatacaccaa atttcaattt    300
acattaatat aaaagataaa aatagaaat atctttttta tagtcacaat aaatttcagt    360
tttgattaaa aaatg                                                     375
```

<210> SEQ ID NO 6
<211> LENGTH: 5508
<212> TYPE: DNA
<213> ORGANISM: Saccharomyces cerevisiae

<400> SEQUENCE: 6

| | |
|---|---|
| atgacagtta gttccgatac aactgctgaa atatcgttag gttggtcaat ccaagactgg | 60 |
| attgatttcc acaagtcatc aagctcccag gcttcactaa ggcttcttga atcactacta | 120 |
| gactctcaaa atgttgcgcc agtcgataat gcgtggatat cgctaatttc aaaggaaaat | 180 |
| ttactgcacc aattccaaat tttaaagagc agagaaaata agaaactct acctctctac | 240 |
| ggtgtcccta ttgctgttaa ggacaacatc gacgttagag gtctacccac caccgctgca | 300 |
| tgtccatcct ttgcatatga gccttccaaa gactctaaag tagtagaact actaagaaat | 360 |
| gcaggtgcga taatcgtggg taagacaaac ttggaccaat ttgccacagg attagtcggc | 420 |
| acacggtctc catatgggaa aacaccttgc gcttttagca aagagcatgt atctggtggt | 480 |
| tcctccgctg ggtcagcatc ggtggtcgcc agaggtatcg taccaattgc attgggtact | 540 |
| gatacagcag ttctggtag agtcccagcc gccttgaaca acctgattgg cctaaagcca | 600 |
| acaaagggcg tcttttcctg tcaaggtgta gttcccgctt gtaaatcttt agactgcgtc | 660 |
| tccatctttg cattaaacct aagtgatgct gaacgctgct ccgcatcat gtgccagcca | 720 |
| gatcctgata atgatgaata ttctagaccc tatgtttcca acccttttgaa aaaattttca | 780 |
| agcaatgtaa cgattgctat tcctaaaaat atcccatggt atggtgaaac caagaatcct | 840 |
| gtactgtttt ccaatgctgt cgaaaatcta tcaagaacgg gcgctaacgt catagaaatt | 900 |
| gattttgagc ctcttttaga gttagctcgc tgtttatacg aaggtacttg ggtggccgag | 960 |
| cgttatcaag ctattcaatc gttttttggac agtaaaccac caaggaaatc tttggaccct | 1020 |
| actgttattt caattataga aggggccaag aaatacagtg cagtagactg cttcagtttt | 1080 |
| gaatacaaaa gacaaggcat cttgcaaaaa gtgagacgac ttctcgaatc agtcgatgta | 1140 |
| ttgtgtgtgc ccacatgtcc tttaaatcct actatgcaac aagttgcgga tgaaccagtc | 1200 |
| ctagtcaatt caagacaagg cacatggact aattttgtca acttggcaga tttggcagcc | 1260 |
| cttgctgttc ccgcagggtt ccgagacgat ggtttgccaa atggtattac tttaatcggt | 1320 |
| aaaaaattca cagattacgc actattagag ttggctaacc gctatttcca aaatatattc | 1380 |
| cccaacggtt ccagaacata cggtactttt acctcttctt cagtaaagcc agcaaacgat | 1440 |
| caattagtgg gaccagacta tgacccatct acgtccataa aattggctgt tgtcggtgca | 1500 |
| catcttaagg gtctgcctct acattggcaa ttggaaaagg tcaatgcaac atatttatgt | 1560 |
| acaacaaaaa catcaaaagc ttaccagctt tttgcttttgc ccaaaaatgg accagtttta | 1620 |
| aaacctggtt tgagaagagt tcaagatagc aatggctctc aaatcgaatt agaagtgtac | 1680 |
| agtgttccaa agaactgtt cggtgctttt atttccatgg ttcctgaacc attaggaata | 1740 |
| ggttcagtgg agttagaatc tggtgaatgg atcaaatcct ttatttgtga agaatctggt | 1800 |
| tacaaagcca aggtacagt tgatatcaca aagtatggtg gatttagagc atattttgaa | 1860 |
| atgttgaaga aaaagagtc ccaaaagaag aagttatttg ataccgtgtt aattgccaat | 1920 |
| agaggtgaaa ttgccgttcg tattatcaag acattaaaaa aattgggtat tagatcagtt | 1980 |
| gcagtttatt ccgaccctga taaatattct caacacgtta ctgatgcaga tgtttctgta | 2040 |
| cccccttcatg gcacaaccgc agcccaaact tatttagaca tgaataagat catagatgcc | 2100 |
| gctaagcaaa ctaatgcaca ggccattatt cctggttatg gtttcttgtc ggaaaatgcg | 2160 |

```
gatttttctg atgcgtgcac cagtgctggc attacctttg ttggtccttc gggagatatt    2220
atcagaggtt tagggttaaa acattctgct agacagattg cacagaaggc tggcgttcct    2280
ctagtgccag gctctttgct tatcacatca gttgaagagg ctaagaaagt cgcagcggaa    2340
ttggaatacc cagttatggt gaagtcaact gctggtggcg gtggtattgg tttgcagaaa    2400
gtcgattctg aagaggacat cgagcatatt tttgagactg tgaaacatca aggtgaaaca    2460
tttttcggtg acgctggtgt atttctggaa cggtttatcg aaaatgccag gcatgttgaa    2520
gtccaactta tgggagatgg ttttggtaag gccattgctt gggcgaacg tgattgttct     2580 ttacagcgtc gtaaccaaaa agttatcgaa gaaactcctg caccaaattt gccagaaaag    2640
acgaggttgg cgttaagaaa ggcagctgaa agtttgggat ctttattgaa ttacaagtgt    2700
gctggtacgg ttgaatttat ttacgatgag aaaaaggacg agttttactt tttagaagtt    2760
aatacaagat tacaagttga acatccaata acagaaatgg ttacagggtt agacttggtc    2820
gagtggatga tcaggattgc cgctaatgat gcacctgatt ttgattctac aaaggtagaa    2880
gtcaatgggg tttcaatgga ggcacgttta tatgctgaaa atccattgaa aaatttcaga    2940
ccttctccag gttacttgt cgatgtgaaa tttcctgatt gggcaagagt ggatacttgg    3000
gttaagaaag gtactaatat ttctcccgaa tatgatccaa cattggccaa aattatcgtt    3060
catgggaaag accgtgatga tgcaatttcc aagttaaatc aagcgttaga agaaacaaaa    3120
gtttacggat gtattactaa cattgactac ctgaagtcta tcattaccag tgatttcttt    3180
gctaaagcaa aagtttctac aaacattttg aactcttatc aatatgagcc taccgccatc    3240
gaaattactt tgcccggtgc acacactagt attcaggatt accccggtag agttgggtac    3300
tggagaattg gtgttccgcc ctctggtcca atggacgcat attcgtttag attggcgaac    3360
agaattgttg gtaatgacta caggactcct gccattgaag taacgttgac tggtccatcc    3420
atcgttttcc attgtgaaac tgtcattgcc attactggtg gtaccgctct atgtacatta    3480
gacggccaag aaattcccca acacaaaccg gtcgaagtta agagggatc tactttatcc    3540 attggcaagt tgacaagcgg ctgtagagca tacttaggta tcaggggtgg cattgatgtg    3600
cctaaatact tgggctctta ttctactttc actctaggaa atgtcggtgg atacaatgga    3660
agggtgctaa aacttggaga cgtactattc ttaccaagca atgaagaaaa taaatcagtt    3720
gagtgccttc cacagaatat tcctcaatca ttaattcctc aaatttccga aactaaggaa    3780
tggagaattg gtgtaacatg tggtccccat gggtctccag attttttaa acctgagtcc    3840 atcgaagaat ttttcagtga gaagtggaag gttcattaca actccaatag atttggtgtc    3900
cgtttgattg gacctaaacc taagtgggca agaagtaatg gtggtgaagg tggtatgcat    3960
ccttcaaaca ctcacgatta cgtttattct ctgggtgcaa ttaatttcac gggtgatgag    4020
ccagttatta ttacttgcga tggtccttcc ttaggtggtt tgtgtgtca agctgttgtc    4080 ccagaagcag aactgtggaa ggttggacag gttaaacccg tgattccat tcagtttgtg    4140 ccactttctt acgaaagctc gagatcctta aggaatctc aggatgttgc aattaaatca    4200
ttggatggta ctaagttaag gcgcttagac tctgtttcaa ttttaccatc attcgaaacg    4260
cctattcttg cacaaatgga aaagtgaat gagctttcac caaggttgt atacagacaa    4320 gcaggtgatc gttatgtttt ggtggaatac ggtgataatg aaatgaattt taatattttcc    4380 tatagaattg aatgcctgat ctcccttgtg aaaaagaata agactattgg tattgttgaa    4440
atgtcccaag gtgttagatc tgtattgata gaatttgatg gttacaaagt cactcaaaaa    4500
gaattgctta agtattggt ggcatatgaa acagaaatcc agtttgatga aaattggaag    4560
```

```
ataacttcta atataataag attaccgatg gctttcgaag actcgaagac tttggcatgt    4620
gttcaaaggt atcaagaaac aattcgttcg tctgctccat ggttgccaaa taacgttgat    4680
ttcattgcca atgtaaatgg aatttcaagg aatgaagttt atgatatgtt gtattctgcc    4740
agatttatgg ttttaggttt aggtgatgtc ttcctagggt cgccttgtgc tgttccatta    4800
gatcctcgtc acagattttt gggaagcaag tacaacccaa gtagaacata tacagaaaga    4860
ggtgcagtcg gtattggcgg tatgtatatg tgcatatatg ctgctaacag tcctggtggg    4920
taccaattag tgggtagaac aataccaatt tgggacaaac tatgtctggc cgcatcttct    4980
gaggttccgt ggttgatgaa cccatttgac caagtcgaat tttacccagt ttctgaagaa    5040
gatttggata aaatgactga agattgtgat aatggtgttt ataaagtcaa tatcgaaaag    5100
agtgtttttg atcatcaaga atacttgaga tggatcaacg caaacaaaga ttccatcaca    5160
gcattccagg agggccagct tggtgaaaga gcagaggaat ttgccaaatt gattcaaaat    5220
gcaaactctg aactaaaaga aagtgtcaca gtcaaacctg acgaggaaga agacttccca    5280
gaaggtgcag aaattgtata ttctgagtat tctgggcgtt tttggaaatc catagcatct    5340
gttggagatt ttattgaagc aggtcaaggg ctactaatta ttgaagccat gaaagcggaa    5400
atgattatat ccgctcctaa atcgggtaag attatcaaga tttgccatgg caatggtgat    5460
atggttgatt ctggtgacat agtggccgtc atagagacat ggcatga              5508
```

<210> SEQ ID NO 7
<211> LENGTH: 1835
<212> TYPE: PRT
<213> ORGANISM: Saccharomyces cerevisiae

<400> SEQUENCE: 7

```
Met Thr Val Ser Ser Asp Thr Thr Ala Glu Ile Ser Leu Gly Trp Ser
1               5                   10                  15

Ile Gln Asp Trp Ile Asp Phe His Lys Ser Ser Ser Gln Ala Ser
            20                  25                  30

Leu Arg Leu Leu Glu Ser Leu Leu Asp Ser Gln Asn Val Ala Pro Val
        35                  40                  45

Asp Asn Ala Trp Ile Ser Leu Ile Ser Lys Glu Asn Leu Leu His Gln
    50                  55                  60

Phe Gln Ile Leu Lys Ser Arg Glu Asn Lys Glu Thr Leu Pro Leu Tyr
65                  70                  75                  80

Gly Val Pro Ile Ala Val Lys Asp Asn Ile Asp Val Arg Gly Leu Pro
                85                  90                  95

Thr Thr Ala Ala Cys Pro Ser Phe Ala Tyr Glu Pro Ser Lys Asp Ser
            100                 105                 110

Lys Val Val Glu Leu Leu Arg Asn Ala Gly Ala Ile Ile Val Gly Lys
        115                 120                 125

Thr Asn Leu Asp Gln Phe Ala Thr Gly Leu Val Gly Thr Arg Ser Pro
    130                 135                 140

Tyr Gly Lys Thr Pro Cys Ala Phe Ser Lys Glu His Val Ser Gly Gly
145                 150                 155                 160

Ser Ser Ala Gly Ser Ala Ser Val Val Ala Arg Gly Ile Val Pro Ile
                165                 170                 175

Ala Leu Gly Thr Asp Thr Ala Gly Ser Gly Arg Val Pro Ala Ala Leu
            180                 185                 190

Asn Asn Leu Ile Gly Leu Lys Pro Thr Lys Gly Val Phe Ser Cys Gln
        195                 200                 205

Gly Val Val Pro Ala Cys Lys Ser Leu Asp Cys Val Ser Ile Phe Ala
```

-continued

```
            210                 215                 220
Leu Asn Leu Ser Asp Ala Glu Arg Cys Phe Arg Ile Met Cys Gln Pro
225                 230                 235                 240

Asp Pro Asp Asn Asp Glu Tyr Ser Arg Pro Tyr Val Ser Asn Pro Leu
                    245                 250                 255

Lys Lys Phe Ser Ser Asn Val Thr Ile Ala Ile Pro Lys Asn Ile Pro
                260                 265                 270

Trp Tyr Gly Glu Thr Lys Asn Pro Val Leu Phe Ser Asn Ala Val Glu
                275                 280                 285

Asn Leu Ser Arg Thr Gly Ala Asn Val Ile Glu Ile Asp Phe Glu Pro
290                 295                 300

Leu Leu Glu Leu Ala Arg Cys Leu Tyr Glu Gly Thr Trp Val Ala Glu
305                 310                 315                 320

Arg Tyr Gln Ala Ile Gln Ser Phe Leu Asp Ser Lys Pro Pro Lys Glu
                    325                 330                 335

Ser Leu Asp Pro Thr Val Ile Ser Ile Ile Glu Gly Ala Lys Lys Tyr
                340                 345                 350

Ser Ala Val Asp Cys Phe Ser Phe Glu Tyr Lys Arg Gln Gly Ile Leu
                355                 360                 365

Gln Lys Val Arg Arg Leu Leu Glu Ser Val Asp Val Leu Cys Val Pro
370                 375                 380

Thr Cys Pro Leu Asn Pro Thr Met Gln Gln Val Ala Asp Glu Pro Val
385                 390                 395                 400

Leu Val Asn Ser Arg Gln Gly Thr Trp Thr Asn Phe Val Asn Leu Ala
                    405                 410                 415

Asp Leu Ala Ala Leu Ala Val Pro Ala Gly Phe Arg Asp Asp Gly Leu
                420                 425                 430

Pro Asn Gly Ile Thr Leu Ile Gly Lys Lys Phe Thr Asp Tyr Ala Leu
                435                 440                 445

Leu Glu Leu Ala Asn Arg Tyr Phe Gln Asn Ile Phe Pro Asn Gly Ser
450                 455                 460

Arg Thr Tyr Gly Thr Phe Thr Ser Ser Val Lys Pro Ala Asn Asp
465                 470                 475                 480

Gln Leu Val Gly Pro Asp Tyr Asp Pro Ser Thr Ser Ile Lys Leu Ala
                485                 490                 495

Val Val Gly Ala His Leu Lys Gly Leu Pro Leu His Trp Gln Leu Glu
                500                 505                 510

Lys Val Asn Ala Thr Tyr Leu Cys Thr Thr Lys Thr Ser Lys Ala Tyr
                515                 520                 525

Gln Leu Phe Ala Leu Pro Lys Asn Gly Pro Val Leu Lys Pro Gly Leu
530                 535                 540

Arg Arg Val Gln Asp Ser Asn Gly Ser Gln Ile Glu Leu Glu Val Tyr
545                 550                 555                 560

Ser Val Pro Lys Glu Leu Phe Gly Ala Phe Ile Ser Met Val Pro Glu
                565                 570                 575

Pro Leu Gly Ile Gly Ser Val Glu Leu Glu Ser Gly Glu Trp Ile Lys
                580                 585                 590

Ser Phe Ile Cys Glu Glu Ser Gly Tyr Lys Ala Lys Gly Thr Val Asp
                595                 600                 605

Ile Thr Lys Tyr Gly Gly Phe Arg Ala Tyr Phe Glu Met Leu Lys Lys
                610                 615                 620

Lys Glu Ser Gln Lys Lys Lys Leu Phe Asp Thr Val Leu Ile Ala Asn
625                 630                 635                 640
```

-continued

```
Arg Gly Glu Ile Ala Val Arg Ile Ile Lys Thr Leu Lys Lys Leu Gly
            645                 650                 655
Ile Arg Ser Val Ala Val Tyr Ser Asp Pro Asp Lys Tyr Ser Gln His
        660                 665                 670
Val Thr Asp Ala Asp Val Ser Val Pro Leu His Gly Thr Thr Ala Ala
    675                 680                 685
Gln Thr Tyr Leu Asp Met Asn Lys Ile Ile Asp Ala Lys Gln Thr
690                 695                 700
Asn Ala Gln Ala Ile Ile Pro Gly Tyr Gly Phe Leu Ser Glu Asn Ala
705                 710                 715                 720
Asp Phe Ser Asp Ala Cys Thr Ser Ala Gly Ile Thr Phe Val Gly Pro
                725                 730                 735
Ser Gly Asp Ile Ile Arg Gly Leu Gly Leu Lys His Ser Ala Arg Gln
            740                 745                 750
Ile Ala Gln Lys Ala Gly Val Pro Leu Val Pro Gly Ser Leu Leu Ile
        755                 760                 765
Thr Ser Val Glu Glu Ala Lys Lys Val Ala Ala Glu Leu Glu Tyr Pro
    770                 775                 780
Val Met Val Lys Ser Thr Ala Gly Gly Gly Ile Gly Leu Gln Lys
785                 790                 795                 800
Val Asp Ser Glu Glu Asp Ile Glu His Ile Phe Glu Thr Val Lys His
                805                 810                 815
Gln Gly Glu Thr Phe Phe Gly Asp Ala Gly Val Phe Leu Glu Arg Phe
            820                 825                 830
Ile Glu Asn Ala Arg His Val Glu Val Gln Leu Met Gly Asp Gly Phe
        835                 840                 845
Gly Lys Ala Ile Ala Leu Gly Glu Arg Asp Cys Ser Leu Gln Arg Arg
    850                 855                 860
Asn Gln Lys Val Ile Glu Glu Thr Pro Ala Pro Asn Leu Pro Glu Lys
865                 870                 875                 880
Thr Arg Leu Ala Leu Arg Lys Ala Ala Glu Ser Leu Gly Ser Leu Leu
                885                 890                 895
Asn Tyr Lys Cys Ala Gly Thr Val Glu Phe Ile Tyr Asp Glu Lys Lys
            900                 905                 910
Asp Glu Phe Tyr Phe Leu Glu Val Asn Thr Arg Leu Gln Val Glu His
        915                 920                 925
Pro Ile Thr Glu Met Val Thr Gly Leu Asp Leu Val Glu Trp Met Ile
    930                 935                 940
Arg Ile Ala Ala Asn Asp Ala Pro Asp Phe Asp Ser Thr Lys Val Glu
945                 950                 955                 960
Val Asn Gly Val Ser Met Glu Ala Arg Leu Tyr Ala Glu Asn Pro Leu
                965                 970                 975
Lys Asn Phe Arg Pro Ser Pro Gly Leu Leu Val Asp Val Lys Phe Pro
            980                 985                 990
Asp Trp Ala Arg Val Asp Thr Trp Val Lys Lys Gly Thr Asn Ile Ser
        995                 1000                1005
Pro Glu Tyr Asp Pro Thr Leu Ala Lys Ile Ile Val His Gly Lys
    1010                1015                1020
Asp Arg Asp Asp Ala Ile Ser Lys Leu Asn Gln Ala Leu Glu Glu
1025                1030                1035
Thr Lys Val Tyr Gly Cys Ile Thr Asn Ile Asp Tyr Leu Lys Ser
    1040                1045                1050
Ile Ile Thr Ser Asp Phe Phe Ala Lys Ala Lys Val Ser Thr Asn
    1055                1060                1065
```

```
Ile Leu Asn Ser Tyr Gln Tyr Glu Pro Thr Ala Ile Glu Ile Thr
    1070                1075                1080

Leu Pro Gly Ala His Thr Ser Ile Gln Asp Tyr Pro Gly Arg Val
    1085                1090                1095

Gly Tyr Trp Arg Ile Gly Val Pro Pro Ser Gly Pro Met Asp Ala
    1100                1105                1110

Tyr Ser Phe Arg Leu Ala Asn Arg Ile Val Gly Asn Asp Tyr Arg
    1115                1120                1125

Thr Pro Ala Ile Glu Val Thr Leu Thr Gly Pro Ser Ile Val Phe
    1130                1135                1140

His Cys Glu Thr Val Ile Ala Ile Thr Gly Gly Thr Ala Leu Cys
    1145                1150                1155

Thr Leu Asp Gly Gln Glu Ile Pro Gln His Lys Pro Val Glu Val
    1160                1165                1170

Lys Arg Gly Ser Thr Leu Ser Ile Gly Lys Leu Thr Ser Gly Cys
    1175                1180                1185

Arg Ala Tyr Leu Gly Ile Arg Gly Gly Ile Asp Val Pro Lys Tyr
    1190                1195                1200

Leu Gly Ser Tyr Ser Thr Phe Thr Leu Gly Asn Val Gly Gly Tyr
    1205                1210                1215

Asn Gly Arg Val Leu Lys Leu Gly Asp Val Leu Phe Leu Pro Ser
    1220                1225                1230

Asn Glu Glu Asn Lys Ser Val Glu Cys Leu Pro Gln Asn Ile Pro
    1235                1240                1245

Gln Ser Leu Ile Pro Gln Ile Ser Glu Thr Lys Glu Trp Arg Ile
    1250                1255                1260

Gly Val Thr Cys Gly Pro His Gly Ser Pro Asp Phe Phe Lys Pro
    1265                1270                1275

Glu Ser Ile Glu Glu Phe Phe Ser Glu Lys Trp Lys Val His Tyr
    1280                1285                1290

Asn Ser Asn Arg Phe Gly Val Arg Leu Ile Gly Pro Lys Pro Lys
    1295                1300                1305

Trp Ala Arg Ser Asn Gly Gly Glu Gly Gly Met His Pro Ser Asn
    1310                1315                1320

Thr His Asp Tyr Val Tyr Ser Leu Gly Ala Ile Asn Phe Thr Gly
    1325                1330                1335

Asp Glu Pro Val Ile Ile Thr Cys Asp Gly Pro Ser Leu Gly Gly
    1340                1345                1350

Phe Val Cys Gln Ala Val Val Pro Glu Ala Glu Leu Trp Lys Val
    1355                1360                1365

Gly Gln Val Lys Pro Gly Asp Ser Ile Gln Phe Val Pro Leu Ser
    1370                1375                1380

Tyr Glu Ser Ser Arg Ser Leu Lys Glu Ser Gln Asp Val Ala Ile
    1385                1390                1395

Lys Ser Leu Asp Gly Thr Lys Leu Arg Arg Leu Asp Ser Val Ser
    1400                1405                1410

Ile Leu Pro Ser Phe Glu Thr Pro Ile Leu Ala Gln Met Glu Lys
    1415                1420                1425

Val Asn Glu Leu Ser Pro Lys Val Val Tyr Arg Gln Ala Gly Asp
    1430                1435                1440

Arg Tyr Val Leu Val Glu Tyr Gly Asp Asn Glu Met Asn Phe Asn
    1445                1450                1455

Ile Ser Tyr Arg Ile Glu Cys Leu Ile Ser Leu Val Lys Lys Asn
```

```
                 1460                1465                1470
Lys Thr Ile Gly Ile Val Glu Met Ser Gln Gly Val Arg Ser Val
    1475                1480                1485
Leu Ile Glu Phe Asp Gly Tyr Lys Val Thr Gln Lys Glu Leu Leu
    1490                1495                1500
Lys Val Leu Val Ala Tyr Glu Thr Glu Ile Gln Phe Asp Glu Asn
    1505                1510                1515
Trp Lys Ile Thr Ser Asn Ile Ile Arg Leu Pro Met Ala Phe Glu
    1520                1525                1530
Asp Ser Lys Thr Leu Ala Cys Val Gln Arg Tyr Gln Glu Thr Ile
    1535                1540                1545
Arg Ser Ser Ala Pro Trp Leu Pro Asn Asn Val Asp Phe Ile Ala
    1550                1555                1560
Asn Val Asn Gly Ile Ser Arg Asn Glu Val Tyr Asp Met Leu Tyr
    1565                1570                1575
Ser Ala Arg Phe Met Val Leu Gly Leu Gly Asp Val Phe Leu Gly
    1580                1585                1590
Ser Pro Cys Ala Val Pro Leu Asp Pro Arg His Arg Phe Leu Gly
    1595                1600                1605
Ser Lys Tyr Asn Pro Ser Arg Thr Tyr Thr Glu Arg Gly Ala Val
    1610                1615                1620
Gly Ile Gly Gly Met Tyr Met Cys Ile Tyr Ala Ala Asn Ser Pro
    1625                1630                1635
Gly Gly Tyr Gln Leu Val Gly Arg Thr Ile Pro Ile Trp Asp Lys
    1640                1645                1650
Leu Cys Leu Ala Ala Ser Ser Glu Val Pro Trp Leu Met Asn Pro
    1655                1660                1665
Phe Asp Gln Val Glu Phe Tyr Pro Val Ser Glu Asp Leu Asp
    1670                1675                1680
Lys Met Thr Glu Asp Cys Asp Asn Gly Val Tyr Lys Val Asn Ile
    1685                1690                1695
Glu Lys Ser Val Phe Asp His Gln Glu Tyr Leu Arg Trp Ile Asn
    1700                1705                1710
Ala Asn Lys Asp Ser Ile Thr Ala Phe Gln Glu Gly Gln Leu Gly
    1715                1720                1725
Glu Arg Ala Glu Glu Phe Ala Lys Leu Ile Gln Asn Ala Asn Ser
    1730                1735                1740
Glu Leu Lys Glu Ser Val Thr Val Lys Pro Asp Glu Glu Glu Asp
    1745                1750                1755
Phe Pro Glu Gly Ala Glu Ile Val Tyr Ser Glu Tyr Ser Gly Arg
    1760                1765                1770
Phe Trp Lys Ser Ile Ala Ser Val Gly Asp Val Ile Glu Ala Gly
    1775                1780                1785
Gln Gly Leu Leu Ile Ile Glu Ala Met Lys Ala Glu Met Ile Ile
    1790                1795                1800
Ser Ala Pro Lys Ser Gly Lys Ile Ile Lys Ile Cys His Gly Asn
    1805                1810                1815
Gly Asp Met Val Asp Ser Gly Asp Ile Val Ala Val Ile Glu Thr
    1820                1825                1830
Leu Ala
    1835
```

MODULATING UREA DEGRADATION IN WINE YEAST

FIELD OF THE INVENTION

The invention is in the field of microbial biochemistry. In one aspect, the invention relates to the manipulation of biochemical pathways involving nitrogen catabolism in organisms capable of fermentation of carbohydrates to produce ethyl alcohol. In selected embodiments, the invention relates to cultures and processes for making wine and other products of fermentation.

BACKGROUND OF THE INVENTION

Arginine is one of the predominant amino acids present in grape musts (Henschke and Jiranek, 1993). Arginine is thought to be transported into the yeast cell by the general amino acid permease encoded by the GAP1 gene (Jauniaux and Grenson, 1990) or by the arginine permease encoded by the CAN1 gene (Hoffmann, 1985). In *Saccharomyces cerevisiae*, arginine is reportedly degraded into urea and ornithine by arginase, the product of the CAR1 gene (Middelhoven, 1964; Sumrada and Cooper, 1982).

The DUR1,2 gene encodes a bifunctional enzyme, urea carboxylase-allophanate hydrolase (Dur1,2; urea amidolyase) which can degrade urea to ammonia and $CO_2$. The urea carboxylase function is encoded separately in the enzyme from green algae, which catalyzes the reaction: ATP+urea+$CO_2$=ADP+phosphate+urea-1-carboxylate (EC 6.3.4.6; systematic name: urea:carbon-dioxide ligase (ADP-forming); other name(s): urease (ATP-hydrolysing); urea carboxylase (hydrolysing); ATP-urea amidolyase; CAS registry number: 9058-98-4; Roon et al., 1970; Roon and Levenberg, 1972; Sumrada and Cooper, 1982). The allophanate hydrolase function is also encoded separately in the enzyme from green algae, which catalyzes the reaction: urea-1-carboxylate+$H_2O$=2 $CO_2$+2 $NH_3$ (EC 3.5.1.54; systematic name: Urea-1-carboxylate amidohydrolase; Other name(s): allophanate lyase; CAS registry number: 79121-96-3; Maitz et al., 1982; Roon, et al., 1972; Sumrada and Cooper, 1982).

In *S. cerevisiae*, the DUR1,2 gene is subject to nitrogen catabolite repression (NCR) by preferred nitrogen sources present in grape must (Genbauffe and Cooper, 1991). Urea that is not degraded may be secreted by yeast cells into the fermenting grape must. Secreted urea can react with ethanol in the must to form ethyl carbamate, which has been shown to produce various benign and malignant tumours in a variety of experimental animals (Mirvisch, 1968) and may therefore be considered a potential health risk to humans.

SUMMARY OF THE INVENTION

In one aspect, the invention relates to the recognition that the concentration of urea in a fermenting grape must, wine or distilled beverage may be controlled by modulating the nitrogen catabolite repression of the DUR1,2 gene in *S. cerevisiae* encoding for urea carboxylase and allophanate hydrolase activities. In one aspect, the invention accordingly provides yeast strains transformed to reduce nitrogen catabolite repression of a gene encoding for urea degrading enzymatic activity expressed by the yeast strain under fermenting conditions. The yeast strain may for example be transformed with a recombinant nucleic acid comprising a coding sequence encoding the urea degrading enzymatic activity, or with a promoter adapted to mediate expression of the urea degrading enzymatic activity under fermenting conditions. In some embodiments, the invention uses native or modified sequences homologous to the *S. cerevisiae* DUR1,2 promoter and coding sequences. The yeast strains and nucleic acids of the invention may for example be used in process to produce fermented alcoholic beverages, such as wines and other products of fermentation.

BRIEF DESCRIPTION OF THE DRAWINGS

FIG. 1 shows a graphic view of the upstream region of the DUR1,2 gene, ending at the start of the DUR1,2 coding sequence and runninng in the 3' to 5' direction (corresponding to SEQ ID NO: 3).The information in the Figure is derived from the published *Saccharomyces cerevisiae* chromosome II complete chromosome sequence (Genbank LOCUS NC_001134, ACCESSION NC_001134, REGION: complement (635670 . . . 643177), VERSION NC_001134.2, GI:14270686; Feldmann, H., Aigle, M., Aljinovic, G., Andre, B., Baclet, M. C., Barthe, C., Baur, A., Becam, A. M., Biteau, N., Boles, E. et al. "Complete DNA sequence of yeast chromosome II" EMBO J. 13 (24), 5795-5809 (1994); Goffeau, A., Barrell, B. G., Bussey, H., Davis, R. W., Dujon, B., Feldmann, H., Galibert, F., Hoheisel, J. D., Jacq, C., Johnston, M., Louis, E. J., Mewes, H. W., Murakami, Y., Philippsen, P., Tettelin, H. and Oliver, S. G. "Life with 6000 genes" Science 274 (5287), 546 (1996)). The Figure also shows an encoded amino acid sequence running from the carboxy to amino direction (corresponding to SEQ ID No: 4).

FIG. 2 sets out the sequence of a portion of the upstream region of the DUR1,2 gene, ending at the DUR1,2 start codon ATG (SEQ ID No: 5). Two putative NCR element GATM(G) boxes are highlighted (one at position −54 to −58 and the other at position −320 to −324), as well as putative TATM boxes.

DETAILED DESCRIPTION OF THE INVENTION

Figure 3:
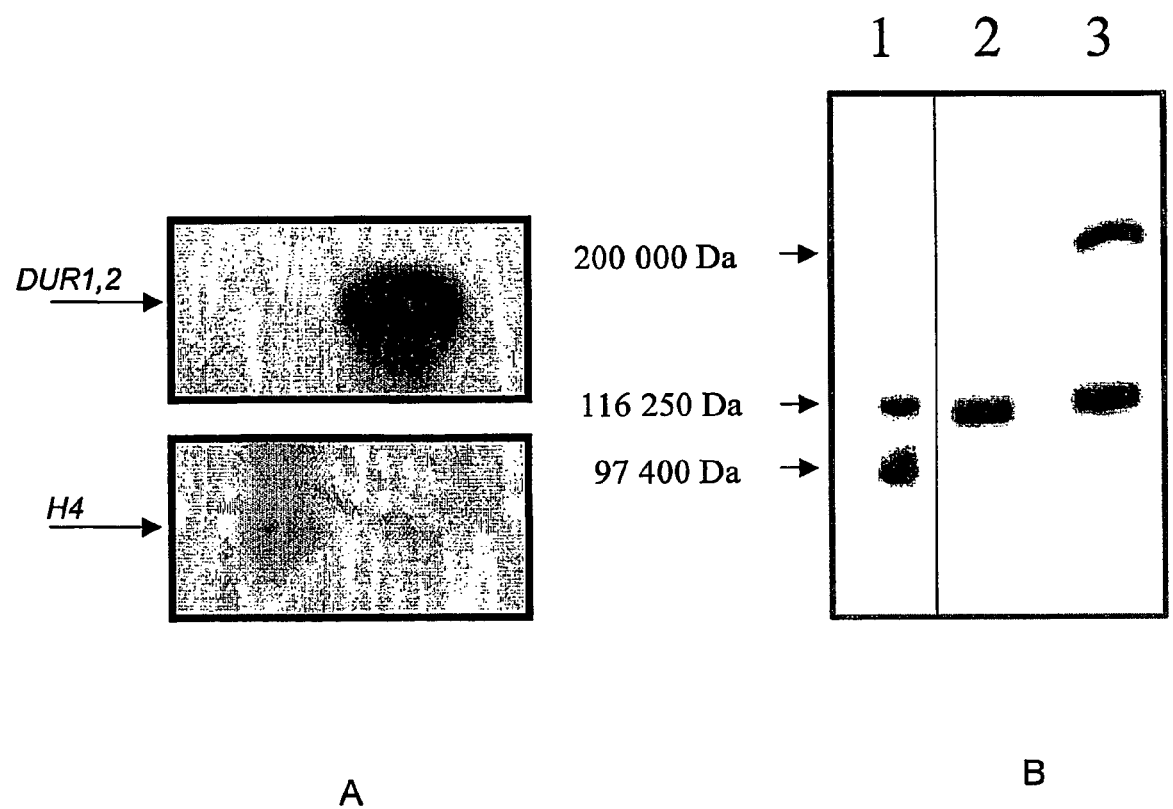
FIG. 3 shows up-regulation of DUR1,2 transcription and translation in yeast engineered with the DUR1,2 expression cassette. (A) DUR1,2 expression in transformed GVY400 cells containing (lane 2) or lacking (lane 1) the DUR1,2 cDNA were compared by Northern analysis of total RNA using $\alpha^{32}$P-dATP labeled probe for DUR 1,2. HHFI encoding histone 4 was used as the RNA loading standard. (B) Urea amidolyase expression in transformed GVY400 cells containing (lane 3) or lacking (lane 2) DUR1,2 cDNA were visualized by a western blot of the biotinylated proteins present in total protein extracted from the transformants. Detection was by chemiluminescence onto X-ray film using streptavidin coupled to horseradish peroxidase. High molecular weight biotinylated standards (5 μg per lane) were included as molecular weight markers (lane 1).
Figure 4:
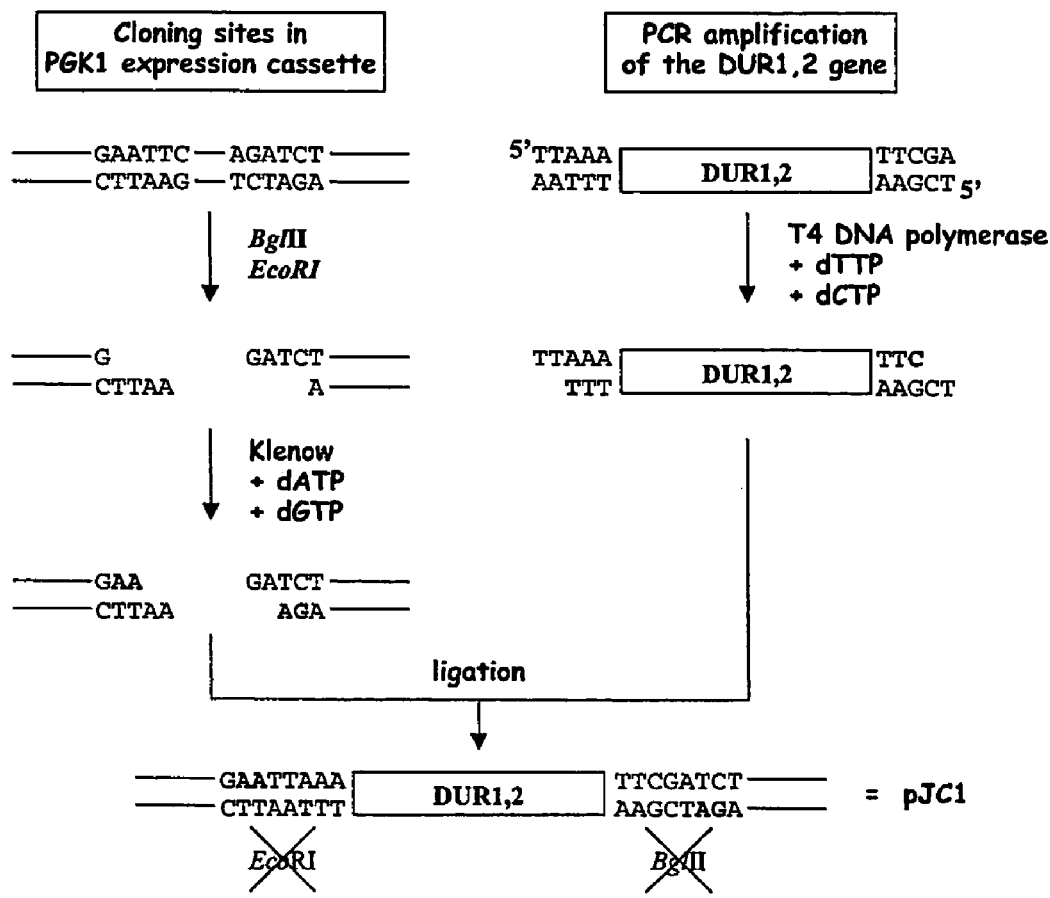
FIG. 4 is a schematic illustration of the cloning strategy of the DUR1,2 gene into the pHVX2 plasmid to yield PJC1, according to the D1/TRISEC method (Dietmaler and Fabry, 1995). Genomic DNA obtained from *S. cerevisiae* TCY 1 was prepared according to standard procedures (Ausubel et al., 1995). The coding sequence of the DUR1,2 gene was amplified by PCR using the ExTaq (Takara) DNA polymerase. The primers used were [5]TTMAMMTGACAGTTAGTTC-CGATACA[3] (SEQ ID NO: 1) for the 5' end and; [5]TCGAM-AAGGTATTTCATGCCMTGTTATGAC[3] SEQ ID NO: 2) for the 3' end of the gene. The designated start codon and the complementary sequence to the stop codon are presented in boldface. The amplification product was treated with T4 DNA polymerase in order to remove some nucleotides on the 3'-flanking end. The 3'-5' exonuclease activity of the enzyme was stopped when required by adding adequate nucleotides. Plasmid pHVX2 (Volschenk et al., 1997) was cut by EcoR1 and BgIII restriction enzymes and then treated with the Klenow fragment of the *E. coli* polymerase I. Restriction sites were partially filled in the presence of dATP and dGTP in order to have sequences compatible with the cloning of the insert.
Figure 5:
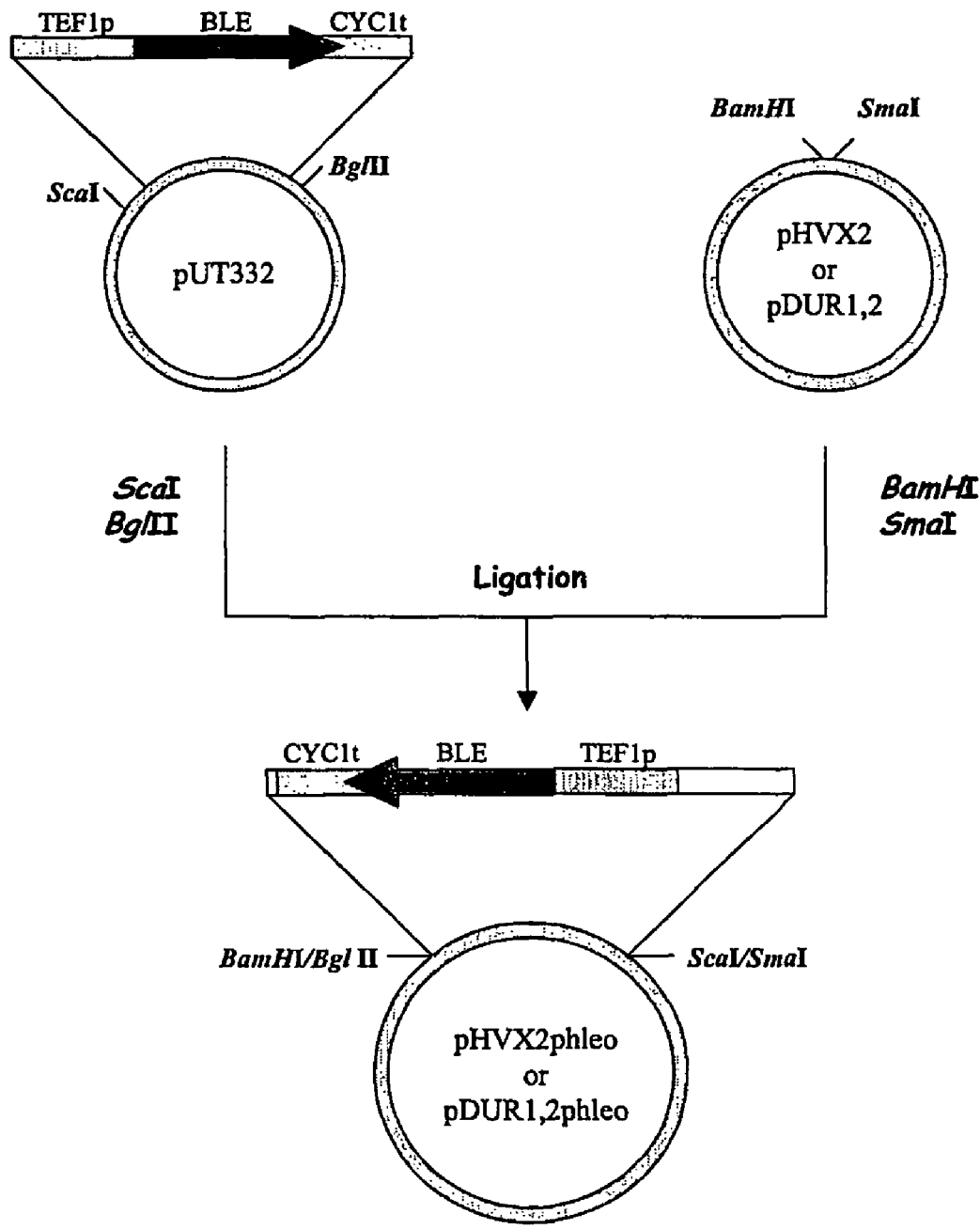
FIG. 5 is a schematic illustration showing the cloning of the phleomycin resistance gene cassette into pJC1 (labeled pHVX2 or pRUR1,2) containing the DUR1,2 gene. Standard recombinant methods were employed to construct pJC2 (labeled pHVX2phleo or pDUR1,2phleo) (Ausubel et al., 1995).
Figure 6:
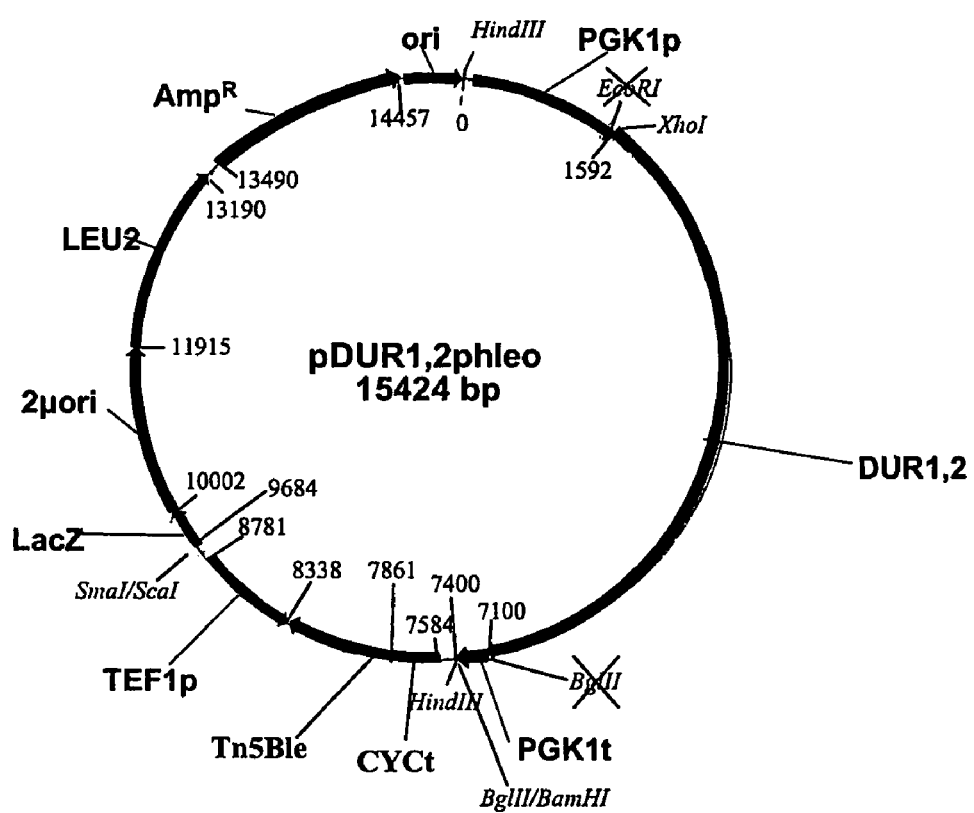
FIG. 6 is a schematic illustration of the plasmid pJC2/DUR1,2phleo (labelled pDUR1,2phleo in the illustration), which is a multicopy, episomal *S. cerevisiae-E. coli* shuttle plasmid derived from the pJC2phleo vector, wherein the DUR1,2 gene is inserted between the regulatory sequences of the yeast phosphoglycerate kinase (PGK1) gene (promoter and terminator sequences). The LEU2 marker facilitates the selection of transformed yeast cells that are auxotrophic for leucine. The plasmid also contains the Tn5Ble gene driven by the constitutive TEF1 yeast promoter and CYC1 yeast terminator. Yeast cells carrying this cassette become resistant to phleomycin. The use of this positive selection marker may be particularly well suited to working with transformed industrial yeast strains that do not carry auxotrophic markers.
Figure 7:
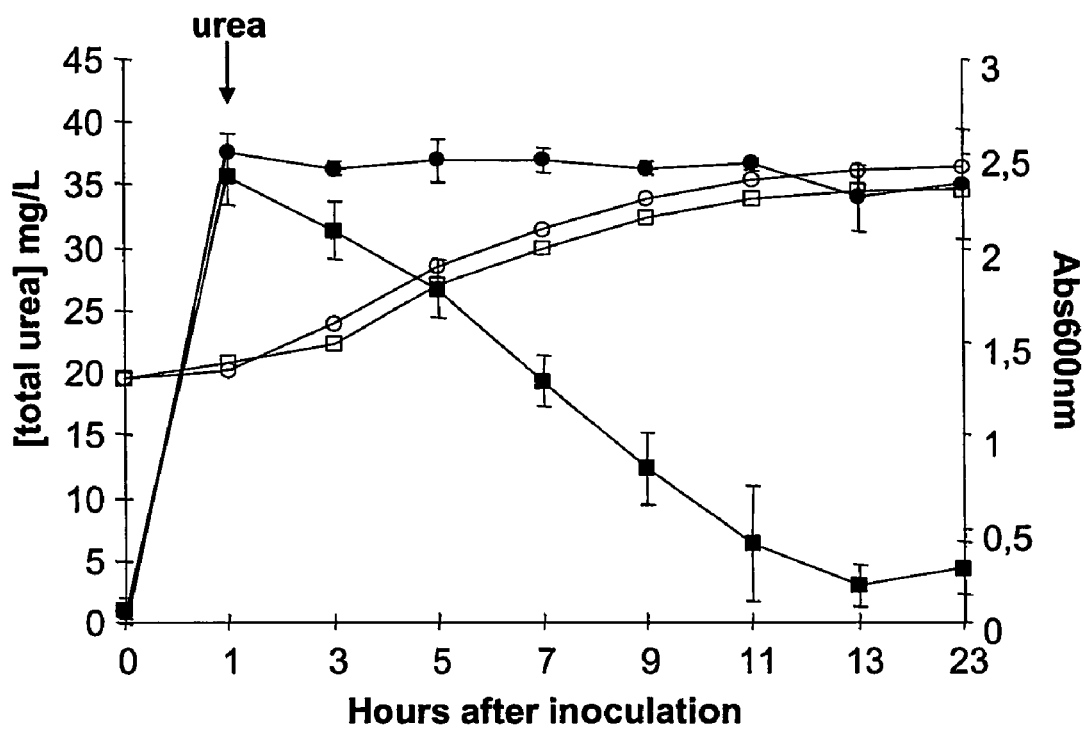
FIG. 7 is a graph showing the ability of transformed yeast of the invention to decrease the concentration of urea in a culture media. A haploid laboratory yeast strain interrupted at the DUR1,2 chromosomal locus was transformed with the pJC2/DUR1,2phleo plasmid or the pJC2phleo plasmid without the DUR1,2 gene. The use of this mutant strain allows the performance of the strain to be evaluated in the absence of background due to a urea amidolyase endogenous activity. Transformed cells were grown in minimal media containing 0.1% glutamine, harvested and used to inoculate fresh media. After 1 hour, 33 mg/L urea were added. Every 2 hours, aliquots of the culture were harvested, cells were broken open in the media with glass beads, and the cell debris removed by centrifugation. Once the supernatent was collected, enzymes were heat inactivated and the urea present in the sample measured. This method facilitates the measurement of intracellular and extracellular urea simultaneously, allowing a distinction to be made between the urea taken up by the cells and the urea metabolised by the cells. The abs600 nm was also regularly measured to check the growth stage of each culture. Standard deviation n=6. Data shown with solid circles is the urea concentration in media innoculated with the laboratory strain transformed with pJC2phleo. Data shown with solid squares is the urea concentration in the media innoculated with the laboratory strain transformed wtih pJC2/DUR1,2phleo. Data shown with empty circles is the abs600 nm of the pJC2phleo strain. Data shown with empty squares is the abs600 nm of the pJC2/DUR1,2phleo strain. The left Y axis is [urea] in mg/L. The right Y axis is abs600 nm. The X axis is hours after innoculation.

In various aspects, the present invention relates to the modification of genes and the use of recombinant genes. In this context, the term "gene" is used in accordance with its usual definition, to mean an operatively linked group of nucleic acid sequences. The modification of a gene in the context of the present invention may include the modification of any one of the various sequences that are operatively linked in the gene. By "operatively linked" it is meant that the particular sequences interact either directly or indirectly to carry out their intended function, such as mediation or modulation of gene expression. The interaction of operatively linked sequences may for example be mediated by proteins that in turn interact with the sequences.

The expression of a gene will typically involve the creation of a polypeptide which is coded for by a portion of the gene. This process typically involves at least two steps: transcription of a coding sequence to form RNA, which may have a direct biological role itself or which may undergo translation of part of the mRNA into a polypeptide. Although the processes of transcription and translation are not fully understood, it is believed that the transcription of a DNA sequence into mRNA is controlled by several regions of DNA. Each region is a series of bases (i.e., a series of nucleotide residues comprising adenosine (A), thymidine Cr), cytidine (C), and guanidine (G)) which are in a desired sequence.

Regions which are usually present in a gene include a promoter sequence with a region that causes RNA polymerase and other transcription factors to associate with the promoter segment of DNA. The RNA polymerase normally travels along an intervening region of the promoter before initiating transcription at a transcription initiation sequence, that directs the RNA polymerase to begin synthesis of mRNA. The RNA polymerase is believed to begin the synthesis of mRNA an appropriate distance, such as about 20 to about 30 bases, beyond the transcription initiation sequence. The foregoing sequences are referred to collectively as the promoter region of the gene, which may include other elements that modify expression of the gene. Such complex promoters may contain one or more sequences which are involved in induction or repression of the gene.

In the context of the present invention, "promoter" means a nucleotide sequence capable of mediating or modulating transcription of a nucleotide sequence of interest in the desired spatial or temporal pattern and to the desired extent, when the transcriptional regulatory region is operably linked to the sequence of interest. A transcriptional regulatory region and a sequence of interest are "operably linked" when the sequences are functionally connected so as to permit transcription of the sequence of interest to be mediated or modulated by the transcriptional regulatory region. In some embodiments, to be operably linked, a transcriptional regulatory region may be located on the same strand as the sequence of interest. The transcriptional regulatory region may in some embodiments be located 5' of the sequence of interest. In such embodiments, the transcriptional regulatory region may be directly 5' of the sequence of interest or there may be intervening sequences between these regions. Transcriptional regulatory sequences may in some embodiments be located 3' of the sequence of interest. The operable linkage of the transcriptional regulatory region and the sequence of interest may require appropriate molecules (such as transcriptional activator proteins) to be bound to the transcriptional regulatory region, the invention therefore encompasses embodiments in which such molecules are provided, either in vitro or in vivo.

The sequence of DNA that is transcribed by RNA polymerase into messenger RNA generally begins with a sequence that is not translated into protein, referred to as a 5' non-translated end of a strand of mRNA, that may attach to a ribosome. This non-translated sequenced (CAP) may be added after transcription of the gene. The mRNA moves through the ribosome until a "start codon" is encountered. The start codon is usually the series of three bases, AUG; rarely, the codon GUG may cause the initiation of translation.

The next sequence of bases in a gene is usually called the coding sequence or the structural sequence. The start codon directs the ribosome to begin connecting a series of amino acids to each other by peptide bonds to form a polypeptide, starting with methionine, which forms the amino terminal end of the polypeptide (the methionine residue may be subsequently removed from the polypeptide by other enzymes). The bases which follow the AUG start codon are divided into sets of 3, each of which is a codon. The "reading frame," which specifies how the bases are grouped together into sets of 3, is determined by the start codon. Each codon codes for the addition of a specific amino acid to the polypeptide being formed. Three of the codons (UAA, UAG, and UGA) are typically "stop" codons; when a stop codon reaches the translation mechanism of a ribosome, the polypeptide that was being formed disengages from the ribosome, and the last preceding amino acid residue becomes the carboxyl terminal end of the polypeptide.

The region of mRNA which is located on the 3' side of a stop codon in a monocistronic gene is referred to as a 3' non-translated region. This region may be involved in the processing, stability, and/or transport of the mRNA after it is transcribed. This region may also include a polyadenylation signal which is recognized by an enzyme in the cell that adds a substantial number of adenosine residues to the mRNA molecule, to form a poly-A tail.

Various genes and nucleic acid sequences of the invention may be recombinant sequences. The term "recombinant" means that something has been recombined, so that with reference to a nucleic acid construct the term refers to a molecule that is comprised of nucleic acid sequences that have at some point been joined together or produced by means of molecular biological techniques. The term "recombinant" when made with reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the naturally-occurring parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated by human intervention using genetic engineering.

Recombinant nucleic acid constructs may for example be introduced into a host cell by transformation. Such recombinant nucleic acid constructs may include sequences derived from the same host cell species or from different host cell species, which have been isolated and reintroduced into cells of the host species.

Recombinant nucleic acid sequences may become integrated into a host cell genome, either as a result of the original transformation of the host cells, or as the result of subsequent recombination and/or repair events. Alternatively, recombinant sequences may be maintained as extra-chromosomal elements. Such sequences may be reproduced, for example by using an organism such as a transformed yeast strain as a starting strain for strain improvement procedures implemented by mutation, mass mating or protoplast fusion. The resulting strains that preserve the recombinant sequence of the invention are themselves considered "recombinant" as that term is used herein.

In various aspects of the invention, nucleic acid molecules may be chemically synthesized using techniques such as are disclosed, for example, in Itakura et al. U.S. Pat. No. 4,598, 049; Caruthers et al. U.S. Pat. No. 4,458,066; and Itakura U.S. Pat. Nos. 4,401,796 and 4,373,071. Such synthetic nucleic acids are by their nature "recombinant" as that term is used herein (being the product of successive steps of combining the constituent parts of the molecule).

Transformation is the process by which the genetic material carried by a cell is altered by incorporation of one or more exogenous nucleic acids into the cell. For example, yeast may be transformed using a variety of protocols (Gietz et al., 1995). Such transformation may occur by incorporation of the exogenous nucleic acid into the genetic material of the cell, or by virtue of an alteration in the endogenous genetic material of the cell that results from exposure of the cell to the exogenous nucleic acid. Transformants or transformed cells are cells, or descendants of cells, that have been genetically altered through the uptake of an exogenous nucleic acid. As these terms are used herein, they apply to descendants of transformed cells where the desired genetic alteration has been preserved through subsequent cellular generations, irrespective of other mutations or alterations that may also be present in the cells of the subsequent generations.

In alternative aspects, the invention relates to yeast strains used in fermentation to produce a variety of products, such as wine, beer, dough, ethanol or vinegar. In alternative embodiments, the invention may for example utilize *S. cerevisiae* yeast strains, *S. bayanus* yeast strains, or *Schizosaccharomyces* yeast strains. Transformed host cells for use in winemaking may for example include strains of *S. cerevisiae* or *Schizosaccharomyces*, such as Bourgovin (RC 212 *Saccharomyces cerevisiae*), ICV D-47 *Saccharamyces cerevisiae*, 71B-1122 *Saccharomyces cerevisiae*, K1V-1116 *Saccharomyces cerevisiae*, EC-1118 *Saccharomyces bayanus*, Vin13, Vin7, N96, and WE352. There are a variety of commercial sources for yeast strains, such as Lallemand Inc. of Montreal Quebec, Canada.

In some embodiments, aspects of the invention may make use of endogenous or heterologous enzymes having urea degrading activity, such as the urea carboxylase and allophanate hydrolase activity of DUR1,2. These enzymes may for example be homologous to DUR1,2 or to regions of DUR1,2 having the relevant activity.

The degree of homology between sequences (such as native DUR1,2 protein or native DUR1,2 nucleic acid sequences and the sequence of an alternative protein or nucleic acid for use in the invention) may be expressed as a percentage of identity when the sequences are optimally aligned, meaning the occurrence of exact matches between the sequences. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, J. Mol. Biol. 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs). The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9,1,0.87); PAM70 (10,1,0.87) BLOSUM80 (10,1,0.87); BLOSUM62 (11,1,0.82) and BLOSUM45 (14,2,0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

Nucleic acid sequences of the invention may in some embodiments be substantially identical, such as substantially identical to DUR1,2 protein or DUR1,2 nucleic acid sequences. The substantial identity of such sequences may be reflected in percentage of identity when optimally aligned that may for example be greater than 50%, 80% to 100%, at least 80%, at least 90% or at least 95%, which in the case of gene targeting substrates may refer to the identity of a portion of the gene targeting substrate with a portion of the target sequence, wherein the degree of identity may facilitate homologous pairing and recombination and/or repair. An alternative indication that two nucleic acid sequences are substantially identical is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in MolecularBiology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in *Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH. Washes for stingent hybridization may for example be of at least 15 minutes, 30 minutes, 45 minutes, 60 minutes, 75 minutes, 90 minutes, 105 minutes or 120 minutes.

It is well known in the art that some modifications and changes can be made in the structure of a polypeptide, such as DUR1,2, without substantially altering the biological function of that peptide, to obtain a biologically equivalent polypeptide. In one aspect of the invention, proteins, urea carboxylase and/or allophanate hydrolase activity may include proteins that differ from the native DUR1,2 sequence by conservative amino acid substitutions. As used herein, the term "conserved amino acid substitutions" refers to the substitution of one amino acid for another at a given location in the protein, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the protein by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6)s are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In alternative embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Bio.* 179:125-142, 184). Genetically encoded hydrophobic amino acids include Gly, Ala, Phe, Val, Leu, Ile, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Tryp.

An apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

It will be appreciated by one skilled in the art that the above classifications are not absolute and that an amino acid may be classified in more than one category. In addition, amino acids can be classified based on known behaviour and or characteristic chemical, physical, or biological properties based on specified assays or as compared with previously identified amino acids.

In various aspects of the invention, the urea degrading activity of a host may be adjusted so that it is at a desired level under fermentation conditions, such as under wine fermentation conditions. The term "fermentation conditions" or "fermenting conditions" means conditions under which an organism, such as *S. cerevisiae*, produces energy by fermentation, i.e. culture conditions under which fermentation takes place. Broadly defined, fermentation is the sum of anaerobic reactions that can provide energy for the growth of microorganisms in the absence of oxygen. Energy in fermentation is provided by substrate-level phosphorylation. In fermentation, an organic compound (the energy source) serves as a donor of electrons and another organic compound is the electron acceptor. Various organic substrates may be used for fermentation, such as carbohydrates, amino acids, purines and pyrimidines. In one aspect, the invention relates to organisms, such as yeast, capable of carbohydrate fermentation to produce ethyl alcohol.

In wine fermentation, the culture conditions of the must are derived from the fruit juice used as starting material. For example, the main constituents of grape juice are glucose (typically about 75 to 150 g/l), fructose (typically about 75 to 150 gA), tartaric acid (typically about 2 to 10 g/l), malic acid (typically about 1 to 8 g/l) and free amino acids (typically about 0.2 to 2.5 g/l). However, virtually any fruit or sugary plant sap can be processed into an alcoholic beverage in a process in which the main reaction is the conversion of a carbohydrate to ethyl alcohol.

Wine yeast typically grows and ferments in a pH range of about 4 to 4.5 and requires a minimum water activity of about 0.85 (or a relative humidity of about 88%). The fermentation may be allowed to proceed spontaneously, or can be started by inoculation with a must that has been previously fermented, in which case the juice may be inoculated with populations of yeast of about $10^6$ to about $10^7$ cfu/ml juice. The must may be aerated to build up the yeast population. Once fermentation begins, the rapid production of carbon dioxide generally maintains anaerobic conditions. The temperature of fermentation is usually from 10° C. to 30° C., and the duration of the fermentation process may for example extend from a few days to a few weeks.

In one aspect, the present invention provides yeast strains that are capable of reducing the concentration of ethyl carbamate in fermented alcoholic beverages. For example, the invention may be used to provide wines having an ethyl carbamate concentration of less than 40 ppb (μg/L), 35 ppb, 30 ppb, 25 ppb, 20 ppb, 15 ppb, 10 ppb or 5 ppb (or any integer value between 50 ppb and 1 ppb). In alternative embodiments, the invention may be used to provide fortified wines or distilled spirits having an ethyl carbamate concentration of less than about 500 ppb, 400 ppb, 300 ppb, 200 ppb, 150 ppb, 100 ppb, 90 ppb, 80 ppb, 70 ppb, 60 ppb, 50 ppb, 40 ppb, 30 ppb, 20 ppb or 10 ppb (or any integer value between 500 ppb and 10 ppb).

In alternative embodiments, the invention may provide yeast strains that are capable of maintaining a reduced urea concentration in grape musts. For example, urea concentrations may be maintained below about 15 mg/l, 10 mg/l, 5 mg/l, 4 mg/l, 3 mg/l, 2 mg/l or 1 mg/l.

In one aspect, the invention provides methods for selecting natural mutants of a fermenting organism having a desired level of urea degrading activity under fermenting conditions. For example, yeast strains may be selected that lacking NCR of DUR1,2. For an example of mutation and selection protocols for yeast, see U.S. Pat. No. 6,140,108 issued to Mortimer et al. Oct. 31, 2000. In such methods, a yeast strain may be treated with a mutagen, such as ethylmethane sulfonate, nitrous acid, or hydroxylamine, which produce mutants with base-pair substitutions. Mutants with altered urea degrading activity may be screened for example by plating on an appropriate medium.

In alternative embodiments, site directed mutagenesis may be employed to alter the level of urea degrading activity in a host. For example, site directed mutagenesis may be employed to remove NCR mediating elements from the DUR1,2 promoter. For example, the GATAA(G) boxes in the native DUR1,2 promoter sequence, as shown in FIG. 2, may be deleted or modified by substitution. In one embodiment, for example, one or both of the GATAA boxes may be modified by substituting a T for the G, so that the sequence becomes TATAA. Methods of site directed mutagenesis are for example disclosed in: Rothstein, 1991; Simon and Moore, 1987; Winzeler et al., 1999; and, Negrittoet al., 1997. In alternative embodiments, the genes encoding for Gln3p and Gat1p that mediate NCR in S. cerevisiae may also be mutated to modulate NCR.

The relative urea degrading enzymatic activity of a yeast strain of the invention may be measured relative to an untransformed parent strain. For example, transformed yeast strains of the invention may be selected to have greater urea degrading activity than a parent strain under fermenting conditions, or an activity that is some greater proportion of the parent strain activity under the same fermenting conditions, such as at least 150%, 200%, 250%, 300%, 400% or 500% of the parent strain activity. Similarly, the activity of enzymes expressed or encoded by recombinant nucleic acids of the invention may be determined relative to the non-recombinant sequences from which they are derived, using similar multiples of activity.

In one aspect of the invention, a vector may be provided comprising a recombinant nucleic acid molecule having the DUR1,2 coding sequence, or homologues thereof, under the control of a heterologous promoter sequence that mediates regulated expression of the DUR1,2 polypeptide. To provide such vectors, the DUR1,2 open reading frame (ORF) from S. cerevisiae may be inserted into a plasmid containing an expression cassette that will regulate expression of the recombinant DUR1,2 gene. The recombinant molecule may be introduced into a selected yeast strain to provide a transformed strain having altered urea degrading activity. In alternative embodiments, expression of a native DUR1,2 coding sequence homologue in a host such as S. cerevisiae may also be effected by replacing the native promoter with another promoter. Additional regulatory elements may also be used to construct recombinant expression cassettes utilizing an endogenous coding sequence. Recombinant genes or expression cassettes may be integrated into the chromosomal DNA of a host such as S. cerevisiae.

Promoters for use in alternative aspects of the invention may be selected from suitable native S. cerevisiae promoters, such as the PGK1 or CAR1 promoters. Such promoters may be used with additional regulator elements, such as the PGK1 and CAR1. terminators. A variety of native or recombinant promoters may be used, where the promoters are selected or constructed to mediate expression of urea degrading activities, such as DUR1,2 activities, under selected conditions, such as wine making conditions.

According to one aspect of the invention, a method of fermenting a carbohydrate is provided, such as a method of fermenting wine, using a host, such as a yeast strain, transformed with a recombinant nucleic acid that modulates the urea degrading activity of the host. For example, the NCR of the DUR1,2 gene may be modulated to enhance the degradation of urea to ammonia and carbon dioxide in a wine making yeast strain. In accordance with this aspect of the invention, fermentation of a grape must with the yeast strain may be carried out so as to result in the production of limited amounts of ethyl carbamate.

In one embodiment, using standard recombinant methods (Ausubel et al., 1995) a phleomycin resistance gene cassette was cloned into a yeast shuttle vector, to produce a plasmid called pJC2phleo. The DUR1,2 gene open reading frame (ORF) was amplified by PCR and cloned into the pJC2phleo plasmid, to produce a vector called pJC2/DUR1,2phleo. The pJC2/DUR1,2phleo vector is a multicopy, episomal S. cerevisiae-E. coli shuttle plasmid in which the DUR1,2 coding sequence is inserted between the regulatory sequences of the yeast phosphoglycerate kinase (PGK1) gene, so that the PGK1 promoter and terminator sequences are operatively linked to the DUR1,2 coding sequence. A LEU2 marker allows the selection of transformed yeast cells that are auxotrophic for leucine. The pJC2/DUR1,2phleo plasmid also contains the Tn5Ble gene driven by the constitutive TEF1 yeast promoter and CYC1 terminator. In vivo analysis of transformants showed that the urea degradation capacity of S. cerevisiae cells transformed with the pJC/DUR1,2phleo plasmid was significantly increased, compared to cells transformed with pJC2phleo, as measured by the concentration of urea in the culture media.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

Entry of the sequence listing is directed into this application. The Sequence Listing material on the compact disc containing file name "80021-398.seq.07.jan.2003.v1.txt," "byte size 4 KB and created on Jan. 7, 2003, is hereby incorporated-by-refernce.

References

The following documents are hereby incorporated by reference:

Ausubel, F. M., Brent, R., Kingston, R. E., Moore, D. D., Seidman, J. G., Smith, J. A., and Struhl, K., editors. 1999. Short Protocols in Molecular Biology, 4$^{th}$ Ed. John Wiley and Sons, N.Y.

Ausubel, F M, Brent, R, Kingston, R E, Moore, D. D., Seidman, J G, Smith, J A, Struhl, K eds. Current Protocols in Molecular Biology. 1987-2000. John Wiley and Sons, Inc.

Dietmaier, W. and Pabry S. (1995). Protocol: DI/tri nucleotide Sticky End Cloning. Boerhinger Mannheim PCR Application Manual.

Genbauffe, F. S., and Cooper, T. G. 1991. The urea amidolyase (DUR1,2) gene of *Saccharomyces cerevisiae*. DNA Seq. 2(1): 19-32.

Gietz, R D, Schiestl, R H, Willems, A R, Woods, R A: Studies on the transformation of intact yeast cells by the LiAc/SS-DNA/PEG procedure. Yeast 11: 355-360 (1995)

Henschke, P. A., and Jiranek, V. 1993. Yeasts: metabolism of nitrogen compounds. In G. H. Fleet, editor. Wine Microbiology and Biotechnology. 77-164, Switzerland: Harwood Academic Publishers.

Hoffrnann, W. 1985 Molecular characterization of the CAN1 locus in *Saccharomyces cerevisiae*: a transmembrane protein without N-terminal hydrophobic signal sequence. J. Biol. Chem. 260(21): 11831-11837.

Jauniaux, J. C., and Grenson, M. 1990. GAP1, the general amino acid permease gene of *Saccharomyces cerevisiae*: nucleotide sequence, protein similarity with the other bakers yeast amino acid permeases, and nitrogen catabolite repression. Eur. J. Biochem. 190(1): 39-44.

Maitz, G. S., Haas, E. M. and Castric, P. A. Purification and properties of the allophanate hydrolase from *Chiamydomonas reinhardii*. Biochim. Biophys. Acta 714 (1982) 486-491.

Middelhoven, W. J. 1964. The pathway of arginine breakdown in *Saccharomyces cerevisiae*. Biochem. Biophys. Acta. 156: 650652.

Mirvish, S. S. 1968. The carcinogenic action and metabolism of urethan and n-hydroxyurethan Adv. Cancer Res. 11: 142.

Negrifto, M T, Wu, X, Kuo, T, Chu, S, Bailis, A M: Influence of DNA sequence identity on efficiency of targeted gene replacement. Mol Cell Biol 17: 278-286 (1997).

Roon, R. J. and Levenberg, B. ATP-Urea amidolyase (ADP) (*Candida utilis*). Methods Enzymol. 17A (1970) 317-324.

Roon, R. J. and Levenberg, B. Urea amidolyase. I. Properties of the enzyme from *Candida utilis*. J. Biol. Chem. 247 (1972) 4107-4113.

Rothstein, R: Targeting, disruption, replacement, and allele rescue: integrative DNA transformation in yeast. Methods Enzymol. 194: 281-301 (1991).

Simon, J R, Moore, P D. Homologous recombination between single-stranded DNA and chromosomal genes in *Saccharomyces cerevisiae*. Mol Cell Biochem 7, pp. 2329-2334.1987.

Sumrada, R. A., and Cooper, T. G. 1982. Urea carboxylase and allophanate hydrolase are components of a multifunctional protein in yeast. J. Biol. Chem. 257(15): 9119-9127.

Volschenk, H., M. Viljoen, M. Grobler, J. Bauer, F. F., Subden, R. E., Denayrolles, M., Lonvaud, A, Young, R. A. & H. J. J. van Vuuren. 1997. Engineering a pathway for malate degradation in *Saccharomyces cerevisiae*. Nature Biotechnol. 15:253-257.

Winzeler, E A, Shoemaker, D D, Astromoff, A, Liang, H, Anderson, K, Andre, B, Bangham, R, Benito, R, Boeke, J D, Bussey, H, Chu, A M, Connelly, C, Davis, K, Dietrich, F, Dow, S W, El Bakkoury, M, Foury, F, Friend, S H, Gentalen, E, Giaever, G, Hegemann, J H, Jones, T, Laub, M, Liao, H, Davis, R W: Functional characterization of the *S. cerevisiae* genome by gene deletion and parallel analysis. Science 285: 901-906 (1999).

---

What is claimed is:

1. A method of making a fermented product comprising maintaining under fermenting conditions a *S. cerevisiae* yeast strain transformed to express a urea degrading enzyme having urea carboxylase and allophanate hydrolase activity from a gene comprising a constitutively active heterologous yeast promoter, and a coding sequence that is at least 80% identical when optimally aligned to a *S. cerevisiae* DUR1,2 coding sequence of SEQ ID NO:6, and wherein the urea degrading enzyme comprises a DUR1,2 protein of SEQ ID NO:7, and wherein the fermented product is selected from the group consisting of alcoholic beverages, distilled alcoholic beverages, wines, beers, doughs, ethanol and vinegar.

2. The method of claim 1, wherein the coding sequence comprises an open reading frame at least 90% identical to the *S. cerevisiae* DUR1,2 coding sequence of SEQ ID NO:6.

3. The method of claim 1, wherein the coding sequence comprises an open reading frame at least 95% identical to the *S. cerevisiae* DUR1,2 coding sequence of SEQ ID NO:6.

4. The method of claim 1, wherein the coding sequence comprises the *S. cerevisiae* DUR1,2 coding sequence of SEQ ID NO:6.

5. The method of claim 2, wherein the coding sequence encodes a DUR1,2 protein of SEQ ID NO:7.

6. The method of claim 3, wherein the coding sequence encodes a DUR1,2 protein of SEQ ID NO:7.

7. The method of claim 1, wherein the fermented product is an alcoholic beverage.

8. The method of claim 2, wherein the fermented product is an alcoholic beverage.

9. The method of claim 3, wherein the fermented product is an alcoholic beverage.

10. The method of claim 4, wherein the fermented product is an alcoholic beverage.

11. The method of claim 1, wherein the fermented product is wine.

12. The method of claim 11, wherein the wine has an ethyl carbamate concentration of less than 30 ppb.

* * * * *